United States Patent [19]

Kleiner

[11] Patent Number: 4,976,740
[45] Date of Patent: Dec. 11, 1990

[54] ANCHORED FEMORAL DOME

[76] Inventor: Jeffrey B. Kleiner, 6031 Tulane St., San Diego, Calif. 92122

[21] Appl. No.: 380,141

[22] Filed: Jul. 14, 1989

[51] Int. Cl.$^5$ .............................................. A61F 2/36
[52] U.S. Cl. ........................................ 623/23; 623/18
[58] Field of Search ....................... 623/16, 18, 20, 19, 623/22, 23; 128/924, 924 K, 924 W, 924 V, 924 T, 924 S, 924 P

[56] References Cited

U.S. PATENT DOCUMENTS 4,224,699  9/1980  Weber ................................... 623/23

FOREIGN PATENT DOCUMENTS 2845231  5/1979  Fed. Rep. of Germany ........ 623/23
0602171  4/1978  U.S.S.R. ........................... 128/924 K
0835433  6/1981  U.S.S.R. ........................... 128/924 F

OTHER PUBLICATIONS

Amstutz, Harlan C., M.D., Tharies ® (Pelvifemoral Resurfacing Prosthesis.
Amstutz, Harlan C., M.D., et al. "Total Hip Articular Replacement by Internal Eccentric Shells", Clinical Orthopedics and Related Research, No. 128, Oct. 1977, pp. 261-284
Charnley, John, "Anchorage of the Femoral Head Prosthesis to the Shaft of the Femur", The Journal of Bone and Joint Surgery, vol. 42B, No. 1, Feb. 1960, pp. 28-30.
Zimmer, The Total System.
Zimmer, The Tharies ® Technique for Surface Replacement, Jan. 1978.
Harris, William H., M.D. Surgical Technique Harris/-Galante Porous Hip Prosthesis, Aug. 1984.

Primary Examiner—David J. Isabella
Attorney, Agent, or Firm—Neil K. Nydegger

[57] ABSTRACT

A prosthetic implant for the head of a femur comprises a substantially hemispherical-shaped dome formed with a hole, and having a relatively flat surface, for abutting a sculpted femoral head having a channel prepared through the bone. A compression bolt is insertable through the hole in the dome and through the prepared channel, with the bolt having a first end engageable with the dome and a second end engageable with a nut and washer to hold the dome firmly in position on the femoral head. The hole in the dome is tapered, and the first end of the compression bolt is correspondingly tapered, for fixed engagement of the bolt with the dome. The dome may include anchoring spikes extending from the bottom surface for embedding the dome in the femoral head to secure the dome on the femoral head. In addition, the bottom surface of the dome is textured to prevent slipping, and skirts may also be provided to form a partial ball-shaped dome. A method is also disclosed for attaching the prosthetic implant to the head of the femur.

12 Claims, 3 Drawing Sheets

ANCHORED FEMORAL DOME

FIELD OF THE INVENTION

This invention pertains generally to prosthetic devices. More particularly, the present invention pertains to prosthetic devices which must be securely anchored to a bone. The present invention is particularly, but not exclusively, useful as a prosthetic extension of the femoral head for use in a hip joint.

BACKGROUND OF THE INVENTION

Over the years, a number of techniques and apparatus have been utilized for securely attaching a prosthetic device to a bone. With respect to total or partial reconstruction of the hip joint, it is desirable to replicate a normal natural hip joint in which the head of the femoral bone that extends from the knee to the pelvis, articulates with the socket (acetabulum) of the hip bone. In such total or partial arthroplasty (surgery for formation of movable joints) it is critical that there be no loosening of the bond between a femoral head prosthesis and living femoral bone.

Known procedures and devices for arthroplasty of the hip include a femoral head prosthesis which is anchored to the shaft of the femoral bone, such as the one disclosed in an article entitled "Anchorage of the Femoral Head Prosthesis to the Shaft of the Femur" by John Charnley published in *The Journal of Bone and Joint Surgery*, Volume 42B, No. 1, February, 1960. In this article, a prosthesis has the shape of a femoral head with a metallic stem. The stem is shaped generally to conform to the internal shape of the femoral bone. In the process, the upper end of the femoral bone is hollowed out sufficiently to provide a cavity. The cavity is then filled with cement, and the stem of the prosthesis is inserted into the cavity to expand the cement and drive it into intimate contact with the internal shape of the bone. This device attempts to prevent loosening of the bond between the femoral head prosthesis and the living bone by providing a large area of contact between the prosthesis and the bone in order to distribute the load as widely as possible. An acrylic cement is used with this device purely as a filling and functions as though it were part of the prosthesis. In essence, the cement acts to fill voids between the prosthesis and the bone to make the combination function as though the stem of the prosthesis were cast in metal to the exact shape and size of the hollowed out cavity. Unfortunately, this technique involves removing large portions of tissue from the femoral canal. In addition, since it uses acrylic cement, it is possible for the cement to wear and loosen upon repeated contact of the weight bearing hip joint. Moreover, such a technique is fairly complicated and involves possible weakening of the bone due to such large tissue removal from the bone. This loss of bone substance makes revision arthroplasty still more complicated and risky.

Owing to complications related to loosening of the components of total hip arthroplasty, as a result of incompetence of the cement interface, uncemented prostheses were developed and then implanted around 1983. These were basically the same design as the cemented arthroplasty except fixation relied on an interference fit between the prosthesis and the medullary cortex of the femur. In addition, various amounts of a porous surface were added to the prosthesis which theoretically would allow for bony ingrowth to help anchor the implant (Morscher, E., "The Cementless Fixation of Hip Endoprostheses", Berlin, Springer-Verlag, 1984). The same problems of massive bone removal, violation of the femoral medullary canal, stress-shielding of the proximal femur (where the implant absorbs the stresses placed on the proximal femur and the unstimulated bone artophies to soft, weakened tissue prone to fracture) remain as well as the new risk of tumor, allergic reaction, and metal ion toxicity due to the increased surface area of metal from the porous surface. (Swensson, O. et al., "Formation of a Fulminant Soft-Tissue Pseudotumor after Uncemented Hip Arthroplasty", J. Bone Joint Surg., 70A, pp. 1238-1242, 1988; Buchert, P. K. et al., "Excessive Metal Release Due to Loosening and Fretting of Sintered Particles on Porous Coated Hip Prostheses", J. Bone Joint Surg., 68A, pp. pp. 606-609, 1986; and Brown, G. C. et al., "Sensitity to Metal as a Possible Cause of Sterile Loosening after Cobalt-Chromium Total Hip Replacement Arthroplasty", J. Bone Joint Surg. 59A, pp. 164-168, 1977). Uncemented implantation of a hip prosthesis has the advantage of avoiding cement fixation but has produced a set of its own unique problems.

The main problem with the described approaches to total hip arthroplasty has to do with the necessity to perform a revision when the patient outlives the implant. The young patient aged thirty to forty (30-40) years who undergoes total hip arthroplasty can anticipate a greater than fifty percent (50%) chance of having a loose prosthesis five (5) years after surgery (Dorr, L. D. et al., "Total Hip Arthroplasty in Patients Less Than 45 Years Old", J. Bone Joint Surg., 65A, pp. 474-479, 1983). Since each successive arthroplasty can be expected to fail earlier (Kavanaugh, B. F. et al., "Revision Total Hip Arthroplasty", J. Bone Joint Surg., 67A, pp. 517-526, 1985) and have a higher risk of infection with each successive operation (Hunter, G. A., "The Results of Revision Total Hip Arthroplasty", J. Bone Joint Surg., 61B, pp. 419-421, 1979), an implant which preserves bony stock (allowing easier revision) such as a cementless load-sharing device is desirable. Such a device which is also relatively risk free with respect to metal ion toxicity would be a useful and unique invention.

Other known techniques and designs are disclosed in an article entitled "Total Hip Articular Replacement by Internal Eccentric Shells" by H. C. Amstutz, et al., *Clinical Orthopedics and Related Research*, No. 128, October, 1977, pp. 261-284. It discloses a number of various design approaches for arthroplasty, including resurfacing the femoral head using cemented metal femoral cups. It also discloses a procedure called the "Tharies" approach, an acronym for Total Hip Articular Replacement by Internal Eccentric Shells. In accordance with the Tharies procedure, portions of the femoral head are removed, as by reaming, to provide notches and an overall shape for accepting a hollow metal femoral shell which is cemented onto the reamed femoral bone. This shell is then implanted in the hip bone of a matching acetabular shell. The device attempts to solve problems related to long term durability of conventional hip replacements including calcaresorbtion, acrylic cracking, prosthetic loosening, and stem fractures. Unfortunately, this technique requires implantation of an acetabular shell in the hip bone. In addition, since acrylic cement is involved, there are problems associated with loosening which may occur whenever a cement-type bonding technique is used.

Further attempts have been made to improve the "Tharies" technique by utilizing a system incorporating a stem-type femoral head prosthesis in combination with matching internal eccentric shells. Known attempts to improve the holding capability have included using standoff pegs to reduce the potential for the stem to bottom out in the cavity which is excised into the femoral bone, and using special coatings on the stem to improve bonding of the cement to the stem.

The present invention recognizes the need for a simple yet effective technique and apparatus for securely anchoring a prosthesis on the head of a femoral bone for use in a joint. The present invention further recognizes the need for an apparatus which firmly holds the prosthesis to the living bone to prevent progressive loosening and failure of the fixation, while avoiding violation of the internal bone canal. The present invention further recognizes the advantages of minimal bone resection, i.e. excision of a portion of the bone. In addition, the present invention is useful as an endoprosthesis alone, or can be utilized in a total hip arthroplasty.

Accordingly, it is an object of the present invention to provide an implant for use as a body joint element which is firmly fixed to the living bone. It is a further object of the present invention to provide an implant which is capable of effectively carrying the load presented on the joint. It is yet another object of the present invention to provide a prosthesis which may be implanted with minimal bone resection. Another object of the present invention is to provide a method and apparatus for simple and efficient implantation of a femoral head prosthesis. Yet another object of the present invention is to provide an implant which is reliable and durable. Still another object of the present invention is to provide a prosthesis which is relatively easy to manufacture and comparatively cost-effective. An additional object of the present invention is to increase the ease with which this prosthesis can be revised to a conventional total hip arthroplasty in the face of the patient outliving the implant.

SUMMARY OF THE INVENTION

A preferred embodiment of the implant for use as a body joint element comprises a substantially hemispherical-shaped dome formed with a radially-oriented hole and having a relatively flat surface for abutting against a sculpted femoral head. A compression bolt is insertable through the hole in the dome and through a channel prepared through the end of the femoral bone. The bolt has a first end engageable with the dome at one end of the channel and a second end opposite the first end engageable with a washer and a nut at the other end of the channel. Engagement of the washer and nut with the bolt holds the compression bolt in place and holds the relatively flat surface of the dome against the femoral head. The hole in the dome is tapered, and the first end of the compression bolt is tapered for fixed engagement of the bolt with the dome. The relatively flat surface of the dome may be formed with a plurality of spikes extending from the surface which are embedable into the prepared surface of the femoral head to secure the dome on the femoral head. Also, the relatively flat surface of the dome may be textured to prevent slipping of the dome relative to the femoral head. In another embodiment, an extension of the dome around the flat surface forms a skirt which may be utilized to project the dome beyond the hemispherical shape to form a partial ball-shaped dome.

The method for attaching the prosthetic extension to the femur requires preparing a channel through the femur which has an exit on the femoral head. The head of the femur is then sculpted to form an abutment substantially centered on the channel. A hemispherical-shaped dome is engaged with a bolt which is inserted through the channel to position the dome over the sculpted femoral head and a fastener is attached to the end of the bolt to draw the dome into fixed engagement with the femoral head. The method may further include mounting a plurality of spikes in the dome and impacting the dome against the femur to embed the spikes in the femoral head and secure the dome to the femoral head.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
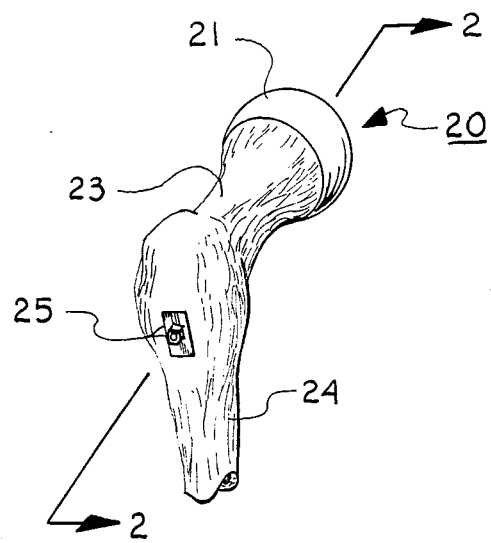
FIG. 1 is a perspective view of an implanted prosthetic extension device assembled and positioned on the head end of the femoral bone in accordance with the present invention.

FIG. 1 shows a prosthetic implant according to the present invention and generally designated 20. In FIG. 1, it is shown in its assembled configuration in position on a femur 24. As perhaps best seen in FIG. 2, the implant 20 comprises a substantially hemispherical-shaped dome 21 which is engageable with a compression bolt 22 that has been inserted through head end 23 of femur 24. The end of compression bolt 22 which is opposite the end that is engaged with the dome 21 is adapted for engagement with a washer 25 and a nut 26. Further illustration of the detailed components of the implant 20 will be best appreciated with reference to components shown in FIGS. 4–9.

Figure 4:
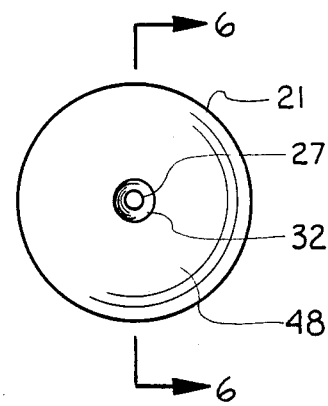
FIG. 4 is a top view of a dome utilized in the prosthetic device in accordance with the present invention.
Figure 5:
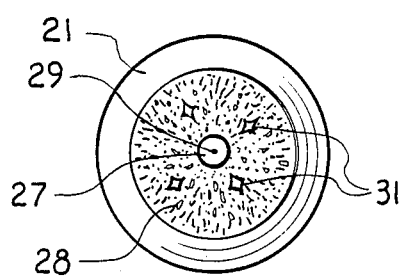
FIG. 5 is a bottom view of the dome shown in FIG. 4.

Referring now to FIG. 4, there is shown a top view of the hemispherical dome 21 having a hole 27 located radially in the center of dome 21. The dome 21 may be made of any suitable material which minimizes the metallic ion exposure to the bone, and is preferably of a material which is proven efficacious for such prosthetic elements, such as cobalt-chromium or titanium alloy. As shown in FIG. 5, the bottom of dome 21 includes a plurality of anchoring spikes 31. In the embodiment shown, there are four (4) such anchoring spikes 31 located at angles equidistant about the longitudinal axis 29 of the dome 21 and spaced radially therefrom. As shown further in FIG. 6, the spikes 31 extend from the flat bottom surface 30 of dome 21 a sufficient distance to ensure they are capable of being embedded into the head end 23 of the femur 24, as will be further described below. In order to increase the holding capability as further described hereinafter, the spikes 31 may be a particular shape, such as the star shape shown. Additionally, in order to further increase the holding capability, the bottom of dome 21 may include a textured surface 28 to allow bony or fibrous ingrowth.

Figure 6:
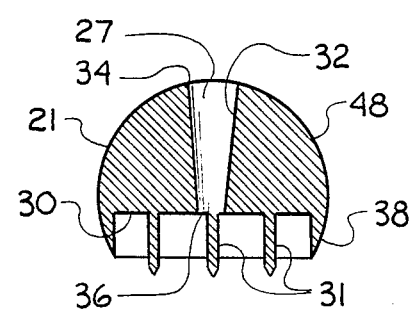
FIG. 6 is a cross-sectional view of the dome as seen along the line 6—6 in FIG. 4.

Also shown in FIG. 6, dome 21 has a hole 27 with a taper 32 so that the top 34 of hole 27 has a larger diameter than the bottom 36 of the hole 27. Also, in the preferred embodiment, the dome 21 includes a skirt 38 which surrounds the lower edge of the generally hemispherical surface of dome 12 to extend the dome beyond the hemispherical shape and to form a partial ball-shaped dome, as generally shown in FIG. 6.

Figure 7:
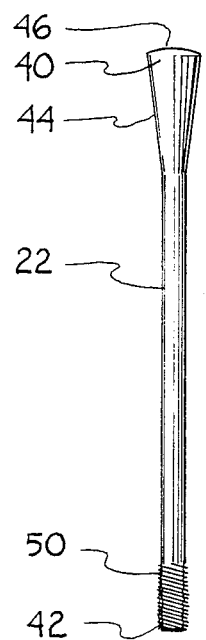
FIG. 7 is a side view of a compression bolt utilized in accordance with the present invention.

Referring now to FIG. 7, it will be seen that compression bolt 22 has a first end 40 which is engageable with dome 21, and a second end 42 which is engageable with washer 25 and nut 26. The compression bolt 14 is generally cylindrical in shape and its first end 40 includes a tapered surface 44, which is correspondingly tapered for engagement with the taper 32 in dome 21. The length of the taper 44 is such that the bolt 22 can be fully seated in dome 21 with the top surface 46 of the bolt 22 flush with the hemispherical-shaped surface 48 of dome 21. The second end 42 of the bolt 22 has a fastening device and, in the embodiment shown, has threads 50 for threadable engagement with nut 26 in cooperation with a washer 25.

Figure 8:
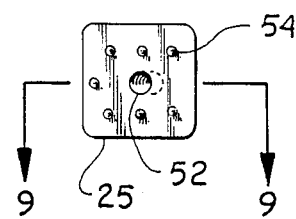
FIG. 8 is a front view of a washer utilized in conjunction with the compression bolt shown in FIG. 7.
Figure 9:
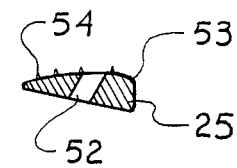
FIG. 9 is a cross-sectional view of the washer as seen along the line 9—9 in FIG. 8.

As shown in FIGS. 8 and 9, the washer 25 has a generally triangular cross section to accommodate the shape of the femur 24 in the general area where it will contact the femur 24. Also, the washer 25 includes a clearance hole 52 which is inclined at an appropriate angle to the surface 53 of washer 25 to conform the surface 53 against the femoral bone 24 at the point of contact. Washer 25 may also include small washer anchoring spikes 54 on surface 53 for engaging washer 25 with the femur 24 as will be more fully described below with respect to the description of the operation of the invention.

Figure 10:
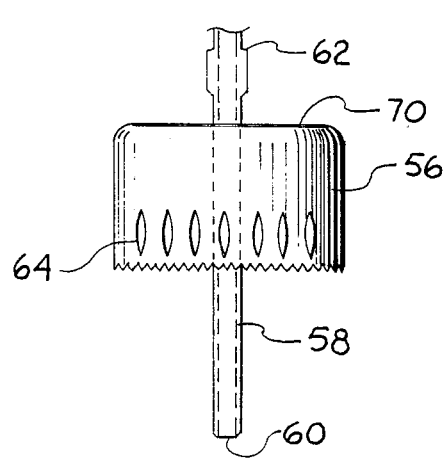
FIG. 10 is a side view of a reamer utilized in accordance with the present invention.
Figure 11:
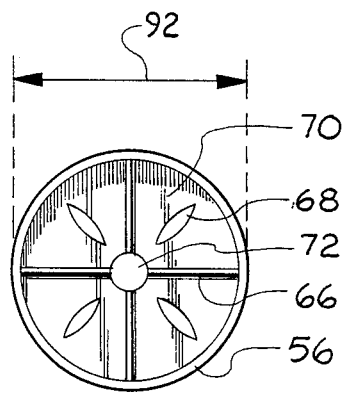
FIG. 11 is a bottom view of the reamer shown in FIG. 10.

Referring now to FIGS. 10 and 11, there is shown a reamer 56 which can be used to remove portions of the head 23 of the femur 24 in preparation for mounting prosthetic implant 20 on femur head 23. The reamer 56 is in the shape of a hollow cylindrical shell which is coaxially aligned in a surrounding relationship with a cannula 58. The cannula 58, which is connected to the reamer 56, has a forward end 60 and a connector end 62 which is operatively engageable with a power drill (not shown). The cannula 58 fits down the previously drilled tunnel 76, which was made with a guide pin and cannulated drill bit (not shown) which are previously placed on head end 23 of the femur 24 and oriented in the desired direction for drilling through and reshaping head end 23. The reamer 56 further includes a plurality of slurry vents 64 which are positioned in the cylindrical wall of the reamer 56. These vents 64 allow bone tissue to be carried away as it is cut by the four (4) equally spaced reaming blades 66 in reamer 56. In the embodiment shown, there are also additional slurry vents 68 in the top 70 of the reamer 56. As will be appreciated, the diameter of the lumen 72 of the cannulated drill bit 58 is of sufficient size to accommodate the bolt 22.

Figure 12:
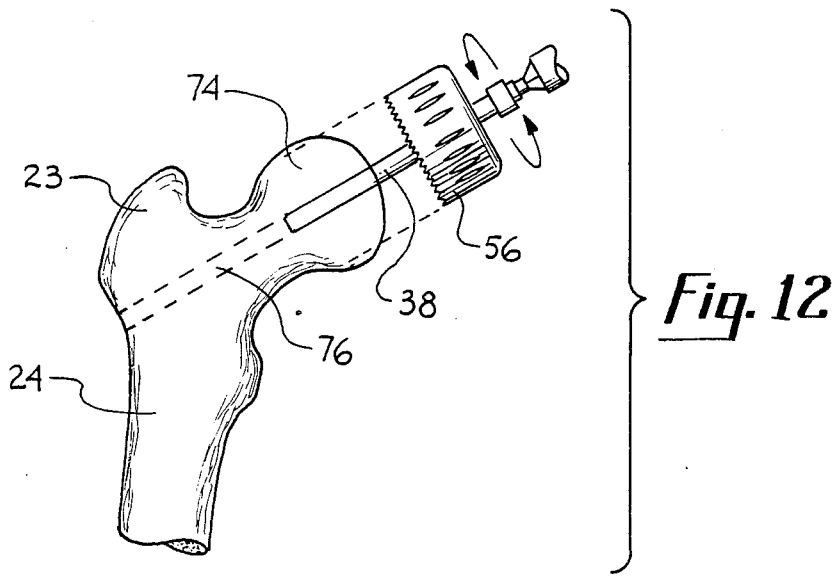
FIG. 12 is a schematic representation of use of the reamer in the end of a femoral bone in accordance with the present invention.
Figure 13:
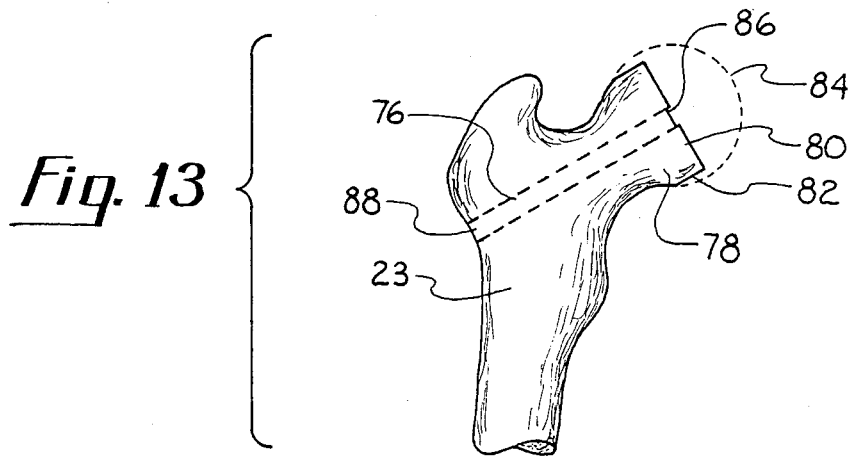
FIG. 13 is a representation as shown by phantom lines of the portion of bone removed from the end of the femoral bone in accordance with the present invention.
Figure 14:
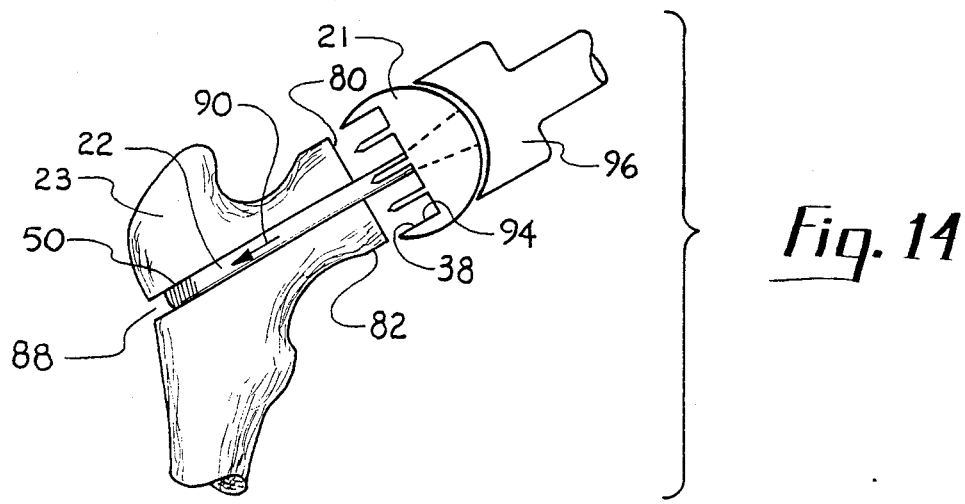
FIG. 14 is a schematic representation of a portion of the method for attaching the prosthetic extension to the femur in accordance with the present invention.

Referring now to FIG. 12 as will be appreciated by the skilled artisan, the meridian of the femoral head 23 may be measured with a sizing ring (not shown) and then marked on the head 74 of end 23 of femoral bone 24. This assures the dome will be properly aligned. As shown in FIG. 12, with the cannula 58 in place, the reamer 56 is rotated to drill the lateral channel 76 through the head end 23 of the femur 24. As the reamer 56 is engaged with head 74, it sculpts the head 74 and excises a portion of the bone to the sculpted-shape head 78 as shown in FIG. 13. In particular, the sculpted head 78 includes a relatively flat abutting surface 80 and a side abutting surface 82. Thus, the bone represented by phantom line 84 has been removed. The bored channel 76 extends through the head end 23 having a first end opening 86 and a second end opening 88. The dome 21 is then engaged with bolt 22 so that the bolt taper 44 is seated firmly in dome taper 32 to fixedly hold the dome 21 on the first end 40 of the bolt 22. The coupled bolt 22 and dome 21 are then positioned on head end 23 with bolt 22 inserted through channel 76 generally in the direction as shown by arrow 90. It is to be noted that the dimension of reamer 56, indicated by the arrows 92 in FIG. 11 corresponds to the inner diameter of the reamer. This dimension is selected so that side abutting surface 82 has a cylindrical shape of the same diameter as the diameter of the inner surface 94 of the skirt 38 of dome 21. A template can then be used to cut the bone at the sites of the anchoring spikes 54 to assist in allowing the anchoring spikes 54 to more easily enter the surface 80 of the sculpted bone and to prevent damage to the bone.

Figure 2:
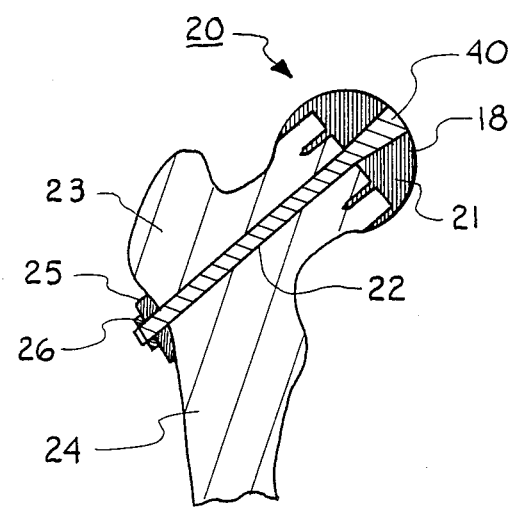
FIG. 2 is a cross-sectional view of the prosthetic device as seen along the line 2—2 in FIG. 1.
Figure 3:
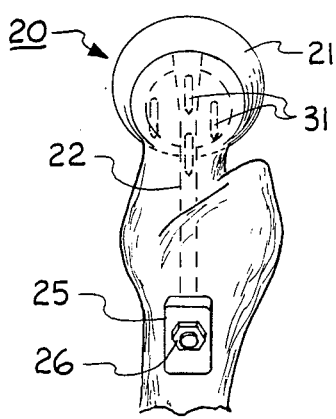
FIG. 3 is an end view, partially in phantom lines, of the assembled implanted prosthetic extension shown in FIG. 1.

An impactor 96 is then utilized to provide force against the top of hemispherical dome 12 to drive the bolt 14 through the channel 76 and bring textured surface 28 into contact with flat surface 80. The impactor can also be used to embed the spikes 54 in the femoral head for securing the dome 21 to the femoral head surface 80. Once dome 21 is satisfactorily in place, the threads 50 of bolt 22 will project from the second open end portion 88 of head end 23 for threaded engagement with nut 26. More specifically, the threads 50 of bolt 22 are inserted through clearance hole 52 of washer 25 to provide for this engagement with nut 26. As nut 26 is advanced on threads 50 of bolt 22, dome 21 is drawn toward the femoral head end 23 to fixedly hold dome 21 on the femoral head end 23, as shown in FIGS. 1 and 2.

It may be readily seen that in accordance with the disclosure for the present invention, the use of implant 20 requires minimal bone resection, yet allows a simple technique for implanting an endoprosthesis onto the bone. Due to the respectively matching surfaces 82 and 94 of the bone 23 and dome 21, dome 21 is securely seated on the sculpted end 78 of the head end 23 of the femoral bone for securely holding the prosthetic extension in place. The load is shared by the end 80 as well as the spikes 54 anchoring the dome 21 in the bone along with the skirts 38 to provide additional strength. Moreover, the compression bolt 22 in cooperation with washer 25 and nut 26 further holds the dome 21 firmly in place to distribute the load throughout the head end 23 of the bone without requiring violation of the femoral canal. In the event a total hip arthroplasty is to be performed, the acetabular portion of the hip joint may then be prepared after the femoral head has been sculpted, i.e. before the dome 21 is placed on the sculpted femoral head 23.

While the particular anchored femoral dome as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. An implant, engageable with a sculpted femoral head having a prepared channel therethrough, for use as a body joint element which comprises:
    a dome, shaped as a solid hemisphere, defining an outer hemispherical bearing surface terminating in a flat lower bone-engaging surface, said dome being formed with a hole, said flat surface of said dome for abutting against said femoral head, said flat surface being textured and having a plurality of spikes extending outwardly therefrom to hold said dome to said sculpted surface; and
    an elongated compression bolt terminating at opposite first and second ends and insertable through said hole and through said prepared channel, said first end including engaging means for attachment to said dome, said second end adapted to be engageable with a fixation means coupled to said second end for holding said flat surface against said sculpted head.

2. An implant as recited in claim 1 wherein said hole in said dome is tapered and said first end of said compression bolt is complimentarily tapered for a fixed engagement of said bolt with said dome.

3. An implant as recited in claim 1 wherein said second end of said compression bolt is threaded and said engageable means comprises a washer having a hole for receiving said second end therethrough and a nut engageable with said second end for holding said washer against said femoral head opposite said dome.

4. An implant as recited in claim 1 further comprising a skirt, said flat surface defining a perimeter, said skirt extending circumferentially around said perimeter and extending distally from said flat surface to extend said dome beyond said hemispherical shape and form a partial ball-shaped dome.

5. A prosthetic extension for the head of a femur which comprises:
    an elongated compression bolt terminating in opposite first and second ends, said bolt being adapted for insertion through a prepared channel in said femur with said first and second ends extending oppositely therefrom;
    a dome shaped as a solid hemisphere defining an outer hemispherical-shaped bearing surface terminating in a flat lower bone-engaging surface, said flat surface of said dome being engageable with said first end to position said dome over said femoral head, said flat surface being textured, said flat surface also being formed with a plurality of spikes extending outwardly from said flat surface, said spikes being embedable in said head of said femur to hold said dome on said head, said first end of said bolt including engaging means for attachment to said dome, said second end adapted to be engageable with a fixation means coupled to said second end for holding said flat surface against said sculpted surface.

6. A prosthetic extension as recited in claim 5 wherein said dome is formed with a tapered hole and said first end of said bolt is complimentarily tapered for a fixed engagement of said bolt with said dome.

7. A prosthetic extension as recited in claim 5 wherein said second end of said compression bolt is threaded and said engaging means comprises a washer having a hole for receiving said second end therethrough and a nut engageable with said second end for holding said washer against said femoral head opposite said dome.

8. A prosthetic extension as recited in claim 5 wherein said dome is made of a material selected from the group comprising cobalt-chromium and titanium.

9. A prosthetic extension as recited in claim 8, wherein said compression bolt and said engageable means are made of a material selected from the group comprising stainless steel and titanium.

10. A method for attaching a prosthetic extension to the femur which comprises the steps of:
    preparing a channel through the femur, said channel being oriented with an exit on the femoral head;
    sculpting the head of the femur to form an abutment substantially centered on said channel;
    engaging a dome shaped as a solid hemisphere defining an outer hemispherical bearing surface terminating in a flat lower bone-engaging surface with an elongated bolt having a first end and a second end to fixedly hold said dome on said first end;
    mounting a plurality of spikes on said flat surface of said dome;
    impacting said dome to embed said spikes in said femoral head for securing said dome to said femoral head;
    inserting said bolt through said channel to position the flat surface of said dome over said sculpted femoral head; and
    engaging an attachment with said second end to hold said dome into fixed engagement with said femoral head.

11. A method for attaching a prosthetic extension to the femur as recited in claim 10 further comprising the step of tightening said attachment to said bolt to draw said dome toward said femoral head and fixedly hold said dome on said femoral head.

12. A method for attaching a prosthetic extension to the femur as recited in claim 10 further comprising the step of forming said bolt, said dome and said attachment from stainless steel.

* * * * *